United States Patent [19]
Gray et al.

[11] Patent Number: 5,777,098
[45] Date of Patent: Jul. 7, 1998

[54] DNA PURIFICATION PROCEDURE

[75] Inventors: Thomas Kevin Gray; Mark A. Doll, both of Grand Forks, N. Dak.

[73] Assignee: University of North Dakota Medical Education Research Foundation, Grand Forks, N. Dak.

[21] Appl. No.: 685,050

[22] Filed: Jul. 23, 1996

[51] Int. Cl.$^6$ ............................ C12P 19/34; C07H 21/00
[52] U.S. Cl. ........................................ 536/25.41; 435/41.1
[58] Field of Search ........................ 435/91.1; 536/25.41

[56] References Cited

U.S. PATENT DOCUMENTS

| | | |
|---|---|---|
| 4,833,239 | 5/1989 | DeBonnville et al. |
| 4,900,677 | 2/1990 | Hewitt. |
| 5,010,183 | 4/1991 | Macfarlane. |
| 5,234,824 | 8/1993 | Mulis. |
| 5,284,940 | 2/1994 | Lin et al. ............................ 536/25.4 |
| 5,346,994 | 9/1994 | Chomczynski. |
| 5,405,951 | 4/1995 | Woodard. |

OTHER PUBLICATIONS

Miller et al. Nucl. Acid Res. 16(3):1215–1217, 1988.

*Primary Examiner*—Gary L. Kunz
*Attorney, Agent, or Firm*—Zarley, McKee, Thomte, Voorhees, & Sease

[57] ABSTRACT

A process and apparatus for purifying DNA which has relatively high molecular weight from a biological sample containing DNA is described. The method comprises the steps (1) lysing the red blood cells in the sample; 2) lysing DNA-containing cells; (3) precipitating the proteins from sample; and (4) and rehydrating and recovering the DNA. method offers the advantages of performance in less than 15 minutes, not requiring organic or poisonous materials, compatibility with most anticoagulants, and requiring less solutions than conventional purification procedures, thus making it simpler and more economical to use.

16 Claims, No Drawings

DNA PURIFICATION PROCEDURE

FIELD OF THE INVENTION

The present invention relates to the field of molecular biology. In particular, the invention is in the area of deoxyribonucleic acid purification.

BACKGROUND OF THE INVENTION

Continued advances in molecular biology and related fields involve the use of deoxyribonucleic acid (DNA) in a variety of forms. For example, advances in the area of recombinant DNA technology continually requires the use of DNA in the form of probes, genomic DNA and plasmid DNA.

In many instances, DNA is available in extremely small amounts, and isolation and purification procedures can be laborious and time consuming. The often time consuming procedures can lead to loss of DNA. In the purification of DNA from specimens obtained from serum, urine and bacterial cultures, there is the added risk of contamination and false positive results.

The purification of DNA from tissue samples often requires chemicals and equipment that are hazardous and/or expensive. Most current methods for DNA preparation use hazardous organic chemicals such as phenol, chloroform, and ammonium alone or in conjunction with absorption columns. Typical DNA purification protocols use high concentrations of caustic and poisonous chaotropic salts such as sodium iodine and sodium perchlorate. Other types of purification procedures use phenol extraction followed by ethanol precipitation. This procedure requires training and technical skills so that DNA is obtained substantially free of proteins and other contaminants.

Further, conventional DNA purification methods often utilize enzymes, such as RNase A and Proteinase K. These enzymes, however, drastically reduce the longevity and shelf life of the purification ingredients.

There are numerous protocols for purifying DNA. As evidenced by recent activity in the area of DNA purification, there is a continued pursuit for optimal DNA purification protocols. For example, U.S. Pat. No. 4,935,342 discloses purification of DNA by selected finding of DNA to anion exchangers in subsequent elution. U.S. Pat. No. 5,010,183 discloses a nucleic acid purification method using a cationic detergent as a solubilizing agent.

More recently, U.S. Pat. No. 5,234,824 to Mullis discloses a method for rapidly purifying DNA in less than about 30 minutes. The method includes the first step of lysing the membranes of the cells using a chemical detergent which is preferably sodium dodecyl sulfate.

Further, Woodard (U.S. Pat. No. 5,405,951) discloses a method for purifying DNA which comprises the addition of a water soluble organic solvent to attach DNA from solution which requires the performance of several time consuming steps.

While the presently available DNA purification procedures are able to achieve their goal, there is a need in the art for a DNA purification procedure which uses no caustic or poisonous compounds and which obtains increased amounts of DNA in a shorter amount of time.

It is therefore a primary objective of the present invention to provide a convenient and reliable technique for purifying large amounts of DNA from biological tissue or cell samples that requires less time than currently available techniques.

It is a further objective of the present invention to provide a DNA purification procedure which does not require the use of caustic or hazardous chemicals.

It is a further objective of the present invention to provide a DNA purification procedure which does not require columns or resins.

It is a further objective of the present invention to provide a DNA purification procedure which does not use unstable enzymes which reduce longevity and shelf life.

It is a further objective of the present invention to provide a DNA purification procedure which is simple and economical to use.

The method and means of accomplishing each of the above objectives as well as others will become apparent from the detailed description of the invention which follows hereinafter.

SUMMARY OF THE INVENTION

The invention relates to a method for rapidly obtaining substantially purified DNA from a biological sample, such as blood, urine, and tissue samples.

The method comprises a first step of lysing the red blood cells with a hypotonic solution in order to release and remove the red cell debris in the sample. The speed of the present invention relies upon this step which lysis the red blood cells faster and more efficiently than conventional methods.

A second step involves lysing the white blood cells/DNA containing cells in the sample with a detergent which destroys the cell membrane and nucleus and releases the DNA from the other cellular components.

A third step involves treatment with chemicals which precipitate the cellular proteins from solution while simultaneously binding the DNA to make it less water soluble. The DNA is then precipitated and can then be rehydrated with a fourth solution.

The present procedure takes less than 15 minutes and yields high molecular weight DNA and further provides several other advantages. First, the procedure does not use hazardous organic chemicals as are commonly used in standard DNA purification procedures. Second, the method does not use unstable enzymes such as RNase A and Proteinase K that drastically reduce the longevity of the ingredients.

Third, the ingredients of the present method are compatible with the three most commonly used anticoagulants. Also, the present procedure uses less solutions than conventional DNA purification procedures and is therefore easier and less expensive to use.

The present invention also contemplates the provision of a kit for use in performing the method of this invention comprising the solutions used in step as described above. The kit can be used for extremely small DNA samples or can be expanded for large-scale use.

DETAILED DESCRIPTION OF THE INVENTION

According to the present invention, a method is provided for rapidly obtaining substantially pure DNA from a biological sample in less than about 15 minutes. The start of any DNA isolation and purification procedure requires obtaining the desired DNA from its source. The source can be any cell-containing biological sample, including blood, urine, stools, biological tissues, etc. The method involves a novel four-step process for treating a biological sample.

The present method can be used to isolate and purify DNA from a variety of biological sources, including animals, bacteria, yeast, and plants.

The method of the present invention comprises a first step of gently lysing the membranes of the red blood cells (non-DNA containing cells) in the biological sample. Lysis herein is the physical disruption of the membranes of the cells. This first step utilizes a hypotonic solution which causes the cell fluids to enter the cell, thereby causing the cell membranes to rupture. The hypotonic solution washes away the hemoglobin present in the red blood cells which can inhibit various restriction enzymes and polymerases.

The hypotonic solution of step one serves the dual functions of lysing the red blood cells and maintaining DNA integrity and stability. The hypotonic solution can simply consist of water. However, the solution preferably contains other hypotonic ingredients as well. The hypotonic solution may first contain a suitable buffer, such as Tris (tris [hydroxymethyl] -aminomethane), which is used to maintain a constant pH of between about 6–8 during the process. A preferred buffer is Tris-HCl. The buffer may be present in a concentration of from 0 to about 100 mM. The most preferred concentration is about 10 parts of a 26 part hypotonic solution.

The hypotonic solution may further contain an agent to enhance the osmolarity of the buffer. Such agents include but are not limited to potassium chloride, sodium chloride, and sodium acetate. The only requirement is that the agent is a salt which can sufficiently maintain a sufficient osmolarity of the buffer. Potassium chloride is a preferred osmolarity agent. The agent may be present in the hypotonic solution in a concentration of from 0 to about 100 mM. The most preferred concentration is 10 parts in a 26 part hypotonic solution.

The next ingredient in the hypotonic solution is a chelating agent which is used to bind calcium and functions to inhibit the clotting mechanism. Commonly used chelating agents include unidentate ligands, polydentate agents, EDTA (ethylenediaminetetraacetic acid) and salts of EDTA. Disodium EDTA is a preferred calcium chelating agent. The chelating agent may be present in the hypotonic solution in a concentration of from 0 to about 20 mM. The most preferred concentration is 2 parts of a 26 part hypotonic solution.

Finally, the hypotonic solution may contain a magnesium containing compound, such as for example $MgCl_2$, $MgSO_4$, and MgOH. It is not important how the magnesium is present in the solution so long as its salt is compatible with the other ingredients of the solution. The magnesium is used to help maintain the stability and integrity of the DNA. $MgCl_2$ is the preferred compound. The concentration of the magnesium compound in the hypotonic solution can range from 0 to about 50 mM. The most preferred concentration is 4 parts in a 26 part hypotonic solution.

The amount of hypotonic solution used is an amount sufficient to lyse the red blood cells in the sample. The minimum amount necessary is about one third of the total amount of biological sample used. There is no upper limit on how much hypotonic solution may be used except for economic considerations.

In the first step, the hypotonic solution is placed in a container and the biological sample is added. The sample and hypotonic solution should then be mixed. If the method is performed in a test tube or microcentrifuge tube, this can easily be accomplished by inverting the tube 10–15 times. The mixture should then be centrifuged. The supernatant will contain the red blood cell debris and possibly lipid material and the pellet will contain the white blood cells/DNA containing cells.

The pellet is preferably washed by adding small amounts of the hypotonic solution and pipeting several times until the pellet is resuspended. This mixture is then centrifuged and the supernatant again removed. This step can be repeated if desired or may be completely eliminated since the purification procedure will still work efficiently even if there is some residual hemoglobin or lipid in the pellet. It should be understood that any of the washing procedures described throughout the purification process may be eliminated if desired since the DNA will still be isolated without doing so. However, it is preferred that the washing steps be performed if there is significant debris in the sample.

The remainder of the sample should then be resuspended in the hypotonic solution with thorough mixing prior to the second step. This can be accomplished by pipeting the hypotonic solution up and down in the sample.

The purpose of the hypotonic solution changes somewhat when the biological sample comprises animal tissues and tissue cultures cells. These samples contain fewer red blood cells but increased amounts of fat, especially when fatty tissues such as brain, breast, and testicular tissues are used. In these instances, the hypotonic solution not only lyses any red blood cells which may be present, but it also removes any lipid material. When working with tissue culture cells, the hypotonic solution serves the exclusive purpose of removing and washing away the tissue culture media.

When isolating DNA from animal tissues and tissue culture cells, the hypotonic solution is not necessary except to resuspend the cells prior to the addition of the solution in the second step. The centrifugation and wash steps described above, however, could be eliminated. Similarly, the volume of hypotonic solution used could be drastically reduced.

The second step of the present method utilizes a detergent-containing solution to lyse the DNA-containing cells which are present in the biological samples. The detergent destroys the cell membrane and nucleus to release the DNA from the other cellular components. The detergent can comprise any anionic detergent. Sodium lauryl sulfate is the preferred detergent. The detergent may be present in a concentration of from about 0.1% to about 20% w/v of an aqueous solution. The amount of detergent solution added in this step is with the range of from about 2 µl for 300 µl of blood, 10–30 mg of tissue and $5 \times 10^5$ to $2 \times 10^6$ tissue culture cells, with economical considerations being the only upper limit. The preferred concentration is about 15 µl for a biological sample as listed above.

The third step of the present method utilizes a solution which is used to precipitate or remove cellular proteins from solution. Simultaneously, the solution contains a salt which binds to the DNA to make it heavier and less soluble in water, yet the DNA does not come out of solution. This precipitating solution comprises a salt capable of precipitating proteins including for example sodium chloride, sodium acetate, potassium chloride, or ammonium acetate to name a few. The preferred precipitating solution is ammonium acetate. The concentration of salt in the precipitating solution is from about 0.1 to about 12 molar. The amount of precipitating solution which may be added is in the range of from about 10 µl up to about 1000 µl when using 300 µl of whole blood, 10–30 mg of tissue or $5 \times 10^5$ to $2 \times 10^6$ tissue culture cells. The preferred amount is 200 µl per sample Once the precipitating solution is added, the ingredient should be mixed.

Following the third step, the proteins are precipitated from the solution with centrifugation. After being centrifuged, the proteins are contained in a pellet and the DNA is in the supernatant. The DNA-containing supernatant is then transferred to a different container wherein the DNA is precipitated from the solution. This can be accomplished by adding isopropyl alcohol or 95% ethanol and mixing. The DNA will appear as visible white thread-like strands. The solution is then centrifuged again such that the DNA is then visible as a small white pellet. As much supernatant as possible should be removed and the centrifugation/removal of supernatant steps can be repeated until only the DNA pellet remains. The DNA pellet can then be washed with 70% ethanol.

The DNA should be allowed to dry. Prior to being used, the DNA should be rehydrated with a rehydration solution. This solution comprises any low mortality buffer that can maintain a pH of from about 6–8 with the addition of a divalent cation chelating agent. Tris-HCl is the preferred low mortality buffer. The divalent cation chelating agent is preferably disodium EDTA but other divalent cation chelating agents as described in step 1 will also work. The concentration of low mortality buffer can be in the range of from about 0.1 to about 100 mM and the concentration of divalent cation chelating agent in the range of from about 0.1 to about 20 mM. The amount of the fourth solution used is not critical since it is only being used for rehydration purposes. The amount can be varied depending upon the concentration of DNA desired.

The above-described solutions are all aqueous. The water used may be purified, distilled, deionized, tap, etc.

The above method steps can be varied in several ways in order to achieve comparable results. For instance, the detergent of step 2 can be combined with the precipitating solution of step 3 to make one solution and expedite the purification process.

The present method offers an advantage in that it does not use any hazardous organic chemicals such as phenol and chloroform. Conventional DNA purification methods commonly require hazardous organic chemicals to isolate and purify DNA.

Also, the present invention can isolate genomic DNA from a biological sample in less than 15 minutes. Prior methods claim times of from 30 minutes to days using similar sample volumes. The present method can perform the same task in less time because the initial buffer used to lyse the red blood cells does so faster and more efficiently. Conventional DNA purification methods use a detergent to lyse the red blood cells and this detergent then interferes with the efficient lyses of the DNA-containing cells in the second step, resulting in a longer incubation time for lysing the DNA-containing cells. Also, the second step lyses the cells more effectively than other methods because the cell pellet is first resuspended in the hypotonic solution prior to the addition of the detergent solution. Without this resuspension process, it is very difficult to resuspend the pellet because it tends to stick together, thus lengthening the amount of time for lysing the DNA containing cells.

In addition, the present invention does not contain any unstable enzymes such as RNase A and Proteinase K that drastically reduce the longevity of the ingredients. Conventional DNA purification methods utilize both of these enzymes. Further, the ingredients used in the present method are autoclavable, indicating very high stability and longshelf life.

The ingredients used in the present method are compatible with the three most commonly used anticoagulants, EDTA, heparin, and citrate. Conventional DNA purification kits recommend the use of only one or two of these different anticoagulants in conjunction with preparing blood samples prior to their purification methods.

Furthermore, the present DNA purification method uses substantially less solutions than conventional methods, thus making the purification procedure simpler to use as well as less expensive.

The start of any DNA purification or isolation procedure requires obtaining the source of the DNA. Typical protocols for obtaining biological samples for DNA purification are well known and routinely carried out. The key to the invention is the ability to purify DNA once obtained from its source.

In order that the invention described herein may be more fully understood, the following examples are set forth. It should be understood that these examples are for illustrative purposes only and are not to be construed as limiting the scope of this invention in any manner.

EXAMPLE 1

DNA Purification Kit

The solutions set forth in the above method can be placed in a convenient DNA purification kit. A standard kit compiled by the inventors is set up to isolate DNA from 0.3 ml of whole blood, 10–30 mg of animal tissue, or $5 \times 10^5$ to $2 \times 10^6$ tissue culture cells. However, any amount of blood, animal tissue, or tissue culture cells could be used by simply increasing or decreasing the amounts of kit components accordingly to the amount of sample used.

The present DNA purification kit is compatible with fresh whole blood stored at 4° C. for less than two months or several years at −70° C. Applicants have used the present invention on isolated genomic DNA from whole blood that was stored at −70° C. for seven years prior to isolation. Similar DNA purification kits recommend the use of only fresh blood less than 2 months old.

The kit components include:

| | |
|---|---|
| Hypotonic solution (S1) - | 230 ml |
| Detergent solution (S2) - | 5 ml |
| Precipitation solution (S3) - | 25 ml |
| Rehydration solution (S4) - | 30 ml |

Other materials used in conjunction with the kit but which are not included are:

sterile 1.5 ml microcentrifuge tubes isopropyl alcohol

70% ethanol waterbath, 65° C.

waterbath, 37° C. (optional)

tissue homogenizer (Fisher cat#15-338-55 or equivalent)

The kit is stable at room temperature (20°–25° C.) for at least 1 year.

Whole blood can be collected in heparin, citrate, or EDTA-coated tubes to prevent clotting and DNA degradation. Blood samples may be stored at 4° C. for 2 months or for years at −70° C. Animal tissues and tissue culture cells can be used fresh or stored for years at −70° C.

EXAMPLE 2

Purification Procedure for Whole Blood (Using Kit)

900 µl of S1 is first added to a sterile 1.5 ml microcentrifuge tube.

300 μl of whole blood is added to the 1.5 ml tube containing the first solution which is then mixed by inverting the tube 10–15 times. This step lyses the red blood cells.

The mixture is centrifuged for 20 seconds at 13,000–15,000×g. As much supernatant is removed as possible without disrupting the white cell pellet. The white cell pellet is washed two times by adding 0.5 ml of the S1 solution and by pipeting up and down until the pellet is resuspended. Again, the mixture is centrifuged at 13,000–15,000×g for 20 seconds to remove as much residual red cell debris as possible since hemoglobin can inhibit the activity of polymerases and restriction enzymes.

The supernatant is removed and discarded. The white cell pellet is then resuspended in 200 μl of S1 solution by pipeting up and down. It is very important that the pellet be completely resuspended prior to adding the S2 solution. 15 μl of S2 solution is added and mixed by finger vortexing.

200 μl of S3 is added and the mixture vortexed for 10–20 seconds. The mixture is then centrifuged at 13,000–15,000×g for three minutes to precipitate the proteins.

The supernatant is transferred to a clean sterile 1.5 ml microcentrifuge tube wherein 400 μl of isopropyl alcohol is added to precipitate the DNA. This is mixed by inverting the tube 10–20 times or until white thread-like strands of DNA form a visible mass. The mixture is then centrifuged for 20 seconds at 13,000–15,000×g at room temperature. The DNA will be visible as a small white pellet.

As much supernatant as possible is removed and the DNA pellet is washed twice by adding 200 μl of 70% ethanol and by inverting the tube several times. This is then centrifuged for 20 seconds at 13,000–15,000×g. The supernatant is carefully removed without disrupting the DNA pellet. If necessary, the pellet can be centrifuged again to remove any remaining liquid.

The DNA pellet is dried by inverting the tube on clean absorbent paper and by air drying for 5–10 minutes.

The DNA is rehydrated by adding 20–100 μl of the fourth solution depending on the concentration of DNA wanted. When dissolved in 20 μl the concentration will be between 0.5–1.0 μg/μl.

EXAMPLE 3

Purification Procedure for Tissue (Using Kit)

This procedure is designed to isolate 5–50 μg of high molecular weight genomic DNA for 10–30 mg of tissue. This protocol has been performed successfully with hamster liver, kidney, heart, brain, tail, bladder, breast, testis, colon, and prostate tissues.

900 μl of S1 solution is added to a vial or tube with a large enough orifice at the top to fit a small tissue homogenizer (such as a 7 ml glass vial).

Approximately 10–30 mg of tissue is added to the vial containing the S1 solution. The tissue is minced with scissors and homogenized until there are no visible chunks of tissue (10–20 sec). Tissues such as brain, breast, and testis have a higher fat content than other tissue and thus more tissue is needed.

The homogenate is transferred to a sterile 1.5 ml microcentrifuge tube and centrifuged for 20 seconds at 13,000–15,000×g. As much supernatant and lipid material as possible is removed and discarded without disrupting the pellet. The pellet is washed twice by adding 0.5 ml of S1 solution and pipeting up and down until the pellet is resuspended. Centrifuge for 20 seconds at 13,000–15,000×g and remove as much residual liquid and lipid material as possible without disrupting the pellet.

The pellet is resuspended in 200 μl of S1 solution by pipeting up and down. 15 μl of S2 solution is added and mixed by finger vortexing (optional: for increased yields from minute amounts of tissues, incubate at 37° C. for 5 minutes after adding S2 solution).

200 μl of S3 solution is next added and the mixture vortexed for 10–20 seconds. It is then centrifuged for 3 minutes at 13,000–15,000×g to precipitate the proteins. The supernatant is then transferred to a clean, sterile, 1.5 ml microcentrifuge tube and 400 μl of isopropyl alcohol is added to precipitate the DNA. The solutions are then mixed by inverting the tube 10–20 times or until white thread-like strands of DNA form a visible mass.

The mixture is next centrifuged for 20 seconds at 13,000–15,000×g at room temperature. The DNA will be visible as a small white pellet. As much supernatant as possible should be removed and the DNA pellet then washed twice by adding 200 μl of 70% ethanol and by inverting the tube several times. The mixture is then centrifuged for 20 seconds at 13,000–15,000×g. As much supernatant as possible should be carefully removed without disrupting the DNA pellet. If necessary, centrifuge the tube again to remove any remaining liquid.

Dry the DNA pellet by inverting the tube on clean absorbent paper and air drying for 5–10 minutes. The DNA can be rehydrated in 50–100 μl of S4 solution and then incubated at 65° C. for 1 hour with periodic mixing by gently tapping on the tube. Store at 4° C.

EXAMPLE 4

Purification Procedure for Tissue Culture Cells
(Using Kit)

This procedure is designed to isolate 5–15 μg of genomic DNA from $5 \times 10^5$ to $2 \times 10^6$ tissue culture cells. The protocol has been successfully tested on rat lymphocytes (Nb2), human lung carcinoma cells (A549), and human cervix carcinoma cells (HeLa).

Between $5 \times 10^5$ to $2 \times 10^6$ or 1.5 ml of cells are transferred to a sterile 1.5 ml centrifuge tube and are centrifuged for 20 seconds at 13,000–15,000×g. If necessary, it is possible to centrifuge more than once to obtain the desired amount of cells.

The pellet is washed once or twice to remove residual tissue culture media by adding 0.5 ml of S1 solution and pipeting up and down until the pellet is resuspended. The suspension is centrifuged for 20 seconds at 13,000–15,000×g and as much residual liquid as possible is removed without disrupting the pellet.

The pellet is resuspended in 200 μl of S1 solution by pipeting up and down. 15 μl of S2 solution is added and mixed by finger vortexing (optional: for increased yield when working with minute amounts of cells, incubate at 37° C. for 5 min).

200 μl of S3 solution is added and vortexed for 10–20 seconds. The mixture is then centrifuged for 3 minutes at 13,000–15,000×g to precipitate the proteins. The supernatant is transferred to a clean, sterile, 1.5 ml microcentrifuge tube and 400 μl of isopropyl alcohol is added to precipitate the DNA. The ingredients are then mixed by inverting the tube 10–20 times or until white thread-like strand of DNA form a visible mass.

The mixture is then centrifuged for 20 seconds at 13,000–15,000×g at room temperature. The DNA will be visible as a small white pellet. As much supernatant as possible is removed and the DNA pellet washed twice by adding 200 µl of 70% ethanol and by inverting the tube several times. The mixture is again centrifuged for 20 seconds at 13,000–15,000×g. As much supernatant as possible is removed without disrupting the DNA pellet. If necessary, centrifuge the tube again to remove remaining liquid.

The DNA pellet is dried by inverting the tube on clean absorbent paper and air drying for 5–10 minutes. The DNA may be rehydrated in 50 µl of S4 solution by incubating at 65° C. for 1 hour with periodic mixing by gently tapping on the tube. The DNA is then stored at 4° C.

The method of the present invention provides a rapid, simple, and reliable way of isolating double-stranded, high molecular weight DNA from whole blood, animal tissue, and tissue culture cells. The purification method can further be used to separate genomic from non-genomic nucleic acid sequences. In addition, the purification method can be adapted for large scale DNA purification from large volumes of lysate from blood, other cells, or tissues.

The present invention also sets forth a kit which is setup to isolate DNA from 0.3 ml of whole blood, 10–30 mg of animal tissue and $5 \times 10^5$ to $2 \times 10^6$ tissue culture cells, however any amount of blood, animal tissue or tissue culture cells could be used by simply increasing or decreasing the kit components accordingly.

It is apparent that many modifications and variations of this invention as set forth above may be made without departing from the spirit and scope. The specific embodiments described are given by way of example only, and the invention is limited only by the terms of the following claims.

What is claimed is:

1. A method for isolating and purifying DNA from a biological sample comprising:
   (a) contacting a DNA-containing biological sample with a hypotonic solution in an amount sufficient to lyse red blood cells and/or remove lipid material contained in the sample;
   (b) removing lysed red blood cells and/or lipid material from the sample;
   (c) resuspending any remaining cells in the sample with the hypotonic solution;
   (d) lysing DNA-containing cells in the sample with a solution consisting essentially of a detergent;
   (e) precipitating the proteins from the sample with a salt;
   (f) removing the supernatant from the sample wherein the supernatant comprises substantially purified DNA.

2. A method according to claim 1 further comprising the step of drying the DNA.

3. A method according to claim 1 wherein steps (a) through (f) can be performed in less than fifteen minutes.

4. A method according to claim 1 wherein the biological sample contains red blood cells and/or lipids and is selected from the group consisting of whole blood, animal tissue, and tissue culture cells.

5. A method according to claim 1 wherein the biological sample is from a source selected from the group consisting of animal, bacteria, yeast, and plant.

6. A method according to claim 1 wherein the hypotonic solution comprises one or more of the following: a buffer, an osmolarity increasing agent, a chelating agent, and a magnesium containing compound.

7. A method according to claim 6 wherein the buffer is Tris-HCl, the osmolarity increasing agent is potassium chloride, the chelating agent is disodium EDTA and the magnesium containing compound is magnesium chloride.

8. A method according to claim 1 wherein the detergent solution is sodium lauryl sulfate.

9. A method according to claim 1 wherein step (e) is performed with a salt selected from the group consisting of ammonium acetate, sodium chloride, sodium acetate, and potassium acetate.

10. A method according to claim 1 wherein the hypotonic solution is water.

11. A method according to claim 1 further comprising the step of:
   (g) precipitating the DNA with from the supernatant with the addition of an alcohol.

12. A method according to claim 11 wherein the alcohol is selected from the group consisting of isopropyl alcohol and 95% ethanol.

13. A method for isolating and purifying DNA from a biological sample containing red blood cells and/or lipids comprising the steps of:
   (a) lysing red blood cells contained in the sample;
   (b) removing lipid material and tissue culture media in the sample;
   (c) lysing DNA-containing cells contained in the sample;
   (d) precipitating the proteins from the sample with a salt; and
   (e) recovering purified DNA from the sample; wherein the steps (a)-(e) are performed without enzymes.

14. A method according to claim 13 wherein the steps can be performed in less than fifteen minutes.

15. A method according to claim 13 wherein steps (c) and (d) are performed by contacting the biological sample with a single solution.

16. A method for isolating and purifying DNA from a biological sample containing DNA-containing cells but not red blood cells or lipids comprising:
   (a) suspending the cells in the sample with a hypotonic solution;
   (b) lysing the cells in the sample with a solution consisting essentially of a detergent;
   (c) precipitating proteins in the sample;
   (d) removing the supernatant from the sample wherein the supernatant comprises substantially purified DNA.

* * * * *